United States Patent [19]

Grandi et al.

[11] Patent Number: 5,047,333
[45] Date of Patent: Sep. 10, 1991

[54] METHOD FOR THE PREPARATION OF NATURAL HUMAN GROWTH HORMONE IN PURE FORM

[75] Inventors: Guido Grandi, Segrate; Elisabetta Franchi, Milan; Federico Maisano, Lodi; Silvia Astrua Testori, Milan, all of Italy

[73] Assignee: Eniricerche S.p.A., Milan, Italy

[21] Appl. No.: 288,358

[22] Filed: Dec. 22, 1988

[30] Foreign Application Priority Data

Dec. 22, 1987 [IT] Italy .................... 23148 A/87

[51] Int. Cl.$^5$ .................. C12P 21/06; C12P 21/02; C12N 15/18; C07K 13/00
[52] U.S. Cl. .................. 435/68.1; 435/69.4; 435/69.7; 435/252.31; 530/399; 935/47; 935/48; 935/74
[58] Field of Search .............. 435/68, 70, 170, 172.3, 435/68.1, 69.1, 69.7; 935/9, 13, 47, 51

[56] References Cited

U.S. PATENT DOCUMENTS 4,532,207 7/1985 Brewer et al. ............... 435/69.1
4,601,980 7/1986 Goeddel et al. ............ 435/172.3 X

FOREIGN PATENT DOCUMENTS 0161937 11/1985 European Pat. Off. .
0306673 7/1988 European Pat. Off. .
WO86/04609 8/1986 PCT Int'l Appl. .
8801534 3/1988 South Africa .

OTHER PUBLICATIONS

Dodet, B., 1990, *Biofutur*, Jun. 1990, pp. 20–29.
Nagai et al, Proc. Nat'l. Academy of Sci. (U.S.A.), vol. 82, pp. 7252–7255 (1985).

Primary Examiner—Richard A. Schwartz
Assistant Examiner—Mary E. Mosher
Attorney, Agent, or Firm—Sughrue, Mion, Zinn Macpeak & Seas

[57] ABSTRACT

An improved method is described for the preparation of natural human growth hormone (hGH) in pure form, which comprises the preparation of a precursor of hGH by means of the culture of *Bacillus subtilis* cells transformed by a hybrid plasmid, the separation of the precursor from the total proteins, the digestion of the precursor with the enzyme Factor Xa and finally the purification of the natural hGH thus obtained from the enzymatic hydrolysis mixture.

5 Claims, 2 Drawing Sheets

METHOD FOR THE PREPARATION OF NATURAL HUMAN GROWTH HORMONE IN PURE FORM

FIELD OF THE INVENTION

The present invention relates to a method for the preparation of a protein obtained in the pure form from recombinant cells. In particular, the present invention concerns an improved method for the preparation of natural human growth hormone (hGH) in pure form and the use of the hormone for human treatment.

BACKGROUND OF THE INVENTION hGH is a protein of 191 amino acids produced in the anterior lobe of the hypophysis throughout the life of an individual, and in greater quantities during the preadult period.

The growth hormone is synthesised in the form of a precursor and, once processed is secreted from the cell.

hGH has for some time been used for curing some forms of dwarfism, which are due to lack of the hormone, and can also be used in the treatment of obesity and for healing burns and wounds.

Until a few years ago, the only source of the hormone was the hypophyses of corpses from which it was extracted at low yields by a complex and expensive method.

Methods have recently been developed for the preparation of hGH by means of fermentation, with the use of host organisms transformed by recombinant DNA techniques.

In particular, GB patent no. 2055982 and EP patent no. 20147 described and claim a method for the preparation of hGH with the use of an engineered strain of *Escherichia coli* (*E. coli*) containing a plasmid which includes the structural sequence of the DNA which codes for the mature protein of 191 amino acids. The sequence is located downstream of a promoter and a ribosome recognition site (RBS) which are necessary for the transcription and translation processes, and juxtaposed to the ATG triplet which codes for methionine.

The presence of the methionine is necessary since it represents the starting signal for the translation of the whole protein.

Known methods, therefore produce a product which is constituted by the amino acid sequence of natural hGH with a methionine (Met) on its amino-terminal.

Although the presence of this amino acid does not seem to affect the activity of the hormone (Olson K. C. et al. (1981), Nature 293, 408), immunological data show that in a fairly high percentage of patients treated with the Met:hGH the appearance of antibodies against the hormone, which prevent extended therapeutic treatment, can be shown.

There is consequently a need to provide a protein identical to the natural one.

Various methods have been proposed in the art for the removal in vivo and in vitro of methionine from the recombinant proteins, and in particular from hGH. On of the in vivo methods is based essentially on the use of signal sequences responsible for the activation of the transport of proteins through the cell membrane of *Escherichia coli* (*E. coli*) or *Bacillus subtilis* (*B. subtilis*).

In general this method comprises the construction of hybrid plasmids containing the nucleotide sequence which codes for mature hGH, fused at its 5' terminal to a sequence which codes for a signal sequence (a leader sequence) and the transformation of host cells by the hybrid plasmids. Suitably grown, the cells produce a fused protein, that is a protein constituted by hGH and the signal sequence. The sequence is then removed at the membrane level by a specific endopeptidase and the mature protein released into the periplasmic space or into the outside environment. In particular, the leader sequences of the protein OmpA (Hsiung H. M. et al. (1986) Biotechnology 4, 991) and the endotoxin of *E. coli* were used for the preparation of mature hGH from transformed *E. coli* cells and the signal sequence of the neutral protease of *B. amyloliquefaciens* was used for the preparation of hGH from *B. subtilis* cells.

However, these known methods have disadvantages resulting on the one hand from the use of *E. coli*, which is a pathogenic organism in man, and on the other hand from the production of an hGH containing from 1 to 4 residual amino acids at its amino-terminus due to the partial processing of the protein expressed by *B. subtilis*.

A second method for removal of the methionine in vitro consists of modification of the gene which codes for a protein so that its synthesis product is constituted by the natural protein and by a longer or shorter peptide sequence which can be removed by treatment with enzymes. In general, this method suffers from the fact that if residual amino acids, which are subject to attack by the enzymes used for the hydrolysis are present in the protein concerned, a greater or lesser percentage of the protein itself is degraded, consequently lowering the production yield.

It is therefore fundamental to provide a specific treatment which enables the fused protein to be hydrolysed exclusively at the point of connection between the product of interest and the amino-terminal peptide.

It is known that Factor Xa, a blood serine protease involved in the complex process of clotting, recognises the Glycine-Arginine (Gly-Arg) sequence, and in particular has a very great affinity for the isoleucine-glutamic acid-glycine-arginine (Ile-Glu-Gly-Arg) tetrapeptide.

Recently, Nagai and collaborators (Nagai, K. et al (1985), Proc. Natl. Acad. Sci. USA 82,7252 have shown that fused products, in which the amino-terminal portion had been positioned to protect the protein of interest from the action of microbial proteases, were processed correctly and specifically when the Ile-Glu-Gly-Arg sequence was positioned at the connecting point.

Whilst enabling the correct processing of the fused proteins and therefore the production of hGH in the natural form, these known methods however have disadvantages resulting from the difficulty of purification of the product obtained.

In fact, the precursor of hGH is difficult to separate both from the pool of proteins produced by the recombinant cells and from the hormone obtained after enzymatic hydrolysis.

SUMMARY OF THE INVENTION

An object of the present invention is therefore constituted by an improved method for the preparation of natural hGH in the pure form.

Another object of the present invention is the use of the hormone for human treatment.

A further object of the present invention is constituted by pharmaceutical compositions containing a therapeutically effective quantity of the hormone thus obtained.

Further objects of the present invention will become clear from a reading of the text and of the examples which follow.

The present invention is based essentially on the finding that the presence of a peptide of a certain length and amino acid composition on the amino-terminal group of the tetrapeptide Ile-Glu-Gly-Arg fused to the N-terminal of hGH enables the hormone to be obtained in the natural form and with a high degree of purity.

In fact, the peptide which still has methionine in position 1, and contains at least one acid i.e. amino acid (glutamic acid, aspartic acid), one basic amino acid (arginine, lysine) or histidine, provides the hGH precursor with characteristics which enable its easy separation, both from the total proteins and from the enzymatic hydrolysis product, by means of known chromatographic techniques.

Moreover, it has been observed that this peptide extension does not affect the specificity of the cutting by Factor Xa, thus enabling the correct processing of the fused protein and the production of the hormone with the correct amino acid sequence.

In particular, the method according to the present invention comprises:

DETAILED DESCRIPTION OF INVENTION a) the preparation by means of the culture of *Bacillus subtilis* cells transformed by a hybrid plasmid, of a precursor of human growth hormone, in which the precursor contains a peptide of a particular length and amino acid composition situated upstream of the tetrapeptide recognised by Factor Xa;

b) the lysis of the cells thus transformed and the separation of the supernatant liquid containing the precursor;

c) the purification of the precursor by chromatography on ion-exchange resin or immobilized metal affinity chromatography (IMAC), and elution with an ionic strength gradient;

d) the hydrolysis of the precursor thus purified with Factor Xa, and finally, e) the separation of the natural hormone with a high degree of purity from the hydrolysis mixture by means of ion-exchange chromatography or immobilized metal affinity chromatography (IMAC).

According to the method of the present invention, the hybrid plasmid was prepared in step a) by the appropriate insertion in an expression vector of a synthetic gene which codes for the hGH precursor.

Vectors suitable for the purpose may be selected from those known in the art.

Preferably used was the vector pSM 214 ATCC 67320, which is characterised by being very stable in *Bacillus subtilis* and capable of inducing the efficient expression of heterologous proteins.

This vector, which is described and claimed in Italian patent application no. 19551 A/87, contains the functional replication origins of pUB110 and pBR322 which enable the replication in *B. subtilis* and in *E. coli* of the km, Bla and Cat genes which code respectively for resistance to kanamycin, ampicillin and chloramphenicol, a strong synthetic promotor which directs the transcription of a dicystronic messenger RNA (mRNA) including the sequences of the Bla and Cat genes, and finally the $t_o$ terminator of the lambda phage of *E. coli* situated downstream of the Cat gene.

This removal from the vector of the Bla gene with EcoRI and HindIII restriction enzymes and the subsequent introduction of a heterologous gene into the site enables the construction of a hybrid plasmid in which the transcription of the gene is ensured by the presence of the single promotor, with selection on chloramphenicol.

According to the present invention, therefore, the heterologous gene is that which codes for a precursor of human growth hormone.

In particular this gene was obtained by the fusion of the 530-base-pair DNA fragment which codes for amino acids 17-191 of hGH to a synthetic oligonucleotide which codes for a polypeptide having the following sequence:

where: (aa) is an amino acid sequence in which the amino acid in position 1 is always methionine, and which includes at least one basic amino acid residue (arginine or lysine) (Arg, Lys), or at least one acidic amino acid residue (glutamic acid or aspartic acid) (Glu, Asp), or Histidine (His) and where n has a value of from 2 to 10.

Ile-Glu-Gly-Arg is the tetrapeptide recognised by Factor Xa, and $hGH_{1-16}$ is the amino-terminal sequence of 16 aminoacids of human growth hormone. Accordingly, and in order to provide an example of the present invention without wishing to limit it, a synthetic oligonucleotide was synthesised which codes for a polypeptide in which the a.a sequence is:

According to the present invention, the 530-bp DNA fragment was obtained from the plasmid pSM209 by digestion with FnuDII and HindIII restriction enzymes and subsequent separation from the digestion mixture by electrophoresis on a polyacrylamide gel.

The aforementioned plasmid pSM 209 was obtained by conventional methods known in the Art, from the commercially available plasmid pUC 9 (Boehringer).

More particularly, the cDNA of hGH was subcloned in plasmid pUC 9, obtaining an intermediate plasmid pWHA41 which was then conventionally treated so as to remove the SmaI restriction site located downstream of the hGH gene, and substitute therefore a Hind III site (for the preparation of the plasmid pSM 209 see Italian Patent Application No. 20345-A/86 the specification of which is hereby incorporated by reference).

More specifically, pSM209 was prepared as follows:

The total RNA was isolated from human pituitary tissue, after which the mRNA (RNA polyadenylate) was separated by affinity chromatography on oligo (dT) cellulose from the total RNA (Edmonds et al., Proc. Natl. Acad. Sci. USA, 68, p. 1336 (1971)). The resulting mRNA was then used to synthesize cDNA in the manner described by Maniatis et al (Molecular Cloning: A Laboratory Manual, p. 217, Cold Spring Harbor 1982).

The resulting hypophysis cDNA molecules were then bonded to HindIII synthetic linkers (Biolabs) and inserted at the HindIII restriction site of plasmid pBR322. The resulting hybrid plasmids (pBR322-cDNA) were used to transform cells of *E. coli* selected for resistance to ampicillin.

The positive colonies were analyzed by the hybridization technique, using a DNA probe complementary with a region of the nucleotide sequence of the hGH gene, thus identifying the clones in which the hybrid plasmid comprises pBR322 and the cDNA of the hGH gene. The cDNA of hGH was isolated from one of these plasmids and sub-cloned in the plasmid pUC9 (Boehringer) thus obtaining plasmid pWHA41.

Next, a HindIII linker was inserted in the plasmid pWHA41 at the end of the cDNA coding for hGH as follows:

0.4 μg of plasmid pWHA41 was cut by one unit of SmaI (Boehringer) for 1.0 hour at 25° C. in 10 μl of buffer containing 15 mM Tris-HCl (pH 8.5), 14 mM KCl, 6.0 mM MgCl$_2$ and 6.0 mM mercaptoethanol. The reaction was stopped by adding EDTA (pH 8.0) up to a final concentration of 20 mM and extracting with phenol-chloroform (1:1 (v/v)) and chloroform-isoamyl (24:1 (v/v)). The DNA was precipitated by adding sodium acetate to the reaction mixture to a final concentration of 0.3 M and 2½ volumes of ethanol, at a temperature of −80° C. for 15 minutes. After centrifuging in an Eppendorf centrifuge, model 5450, the precipitate was separated, dried in vacuo and resuspended in a buffer containing 66 mM Tris-HCl (pH 7.6), 1.0 mM ATP, 1.0 mM spermidine, 10 mM MgCl$_2$, 15 mM dithiothreitol (DTT) and 0.2 mg/ml of calf serum albumin (BSA).

1.0 μg of HindIII d(GAAGCTTC) (Boehringer) linker was phosphorylated in 10 μl of a buffer containing 66 mM Tris-HCl (pH 7.6), 1.0 mM ATP, 1.0 mM spermidine, 10 mM MgCl$_2$, 15 mM DTT, 0.2 mg/ml BSA and 2 units of T4 DNA kinase (Biolabs) and incubated for 1.0 hour at 37° C. The reaction mixture was then added to 10 μl of the same solution containing pWHA41 cut with SmaI and incubated in the presence of 1.0 unit of T4 DNA ligase for 14 hours at 23° C. The reaction was stopped by adding 1.0 μl of a solution containing 0.5 M EDTA (pH 8.0), extracted once with phenol-chloroform and once with chloroform-isoamyl and precipitated with 2½ volumes of ethanol after adding sodium acetate to the solution up to a final concentration of 0.3M. The solution was kept at 80° C. for 15 minutes and then centrifuged for 15 minutes. The thus-separated DNA was resuspended in 100 μl of a buffer containing 50 mM Tris-HCl (pH 8.0), 10 mM MgCl$_2$, 50 mM NaCl and 20 units of HindIII (Boehringer) enzyme and incubated for 2 hours and 30 minutes at 37° C. The reaction was stopped by extraction with phenol-chloroform and chloroform-isoamyl and the DNA was precipitated by adding 2½ volumes of ethanol after adding sodium acetate to the solution up to a final concentration of 3.0M. After centrifuging, the DNA was resuspended in 50 ml of a solution containing 10 mM Tris-HCl (pH 8.0), 1.0 mM EDTA and 100 mM NaCl and placed on a Sephadex G50 (2 ml) column brought to equilibrium in the same buffer. The eluted DNA was precipitated as described hereinbefore and resuspended in 20 μl of a buffer containing 50 mM Tris-HCl (pH 7.6), 10 mM MgCl$_2$, 10 mM DTT, 1.0 mM ATP and 1.0 unit of T4 DNA ligase (Boehringer) and incubated for 14 hours at 14° C. The reaction was inactivated for 10 minutes at 70° C. and then used (1 ng of DNA) to transform 0.3 ml of competent cells of E. coli JM101 (BRL). 12 white Amp$^R$ colonies were isolated from the recombinant substances, obtained by selection on LB (DIFCO) plates containing 50 μg/ml of ampicillin.

The 12 colonies were examined by rapid extraction of plasmid DNA by the method described by Rodriguez and Tait ("Recombinant DNA Techniques: An Introduction", pp. 50-51, Addison-Wesley Publishing Company). 1/20 of the resulting DNA was cut with one unit of HindIII restriction enzyme in 10 μl of the previously-described reaction mixture and incubated for 30 minutes at 37° C. After the enzyme had been inactivated at 70° C. for 10 minutes, the DNA was placed on 0.8% agarose gel and subjected to 100 V for 2.0 hours. All 12 colonies contained the HindIII restriction site at the position of the SmaI site. As expected, digestion of DNA resulted in two fragments, one of which contained about 690 base pairs and was the hGH gene.

One of the clones, called JM101 (pSM209) was chosen for further analysis and the plasmid DNA isolated therefrom, called pSM209, was extracted by the procedure described by Maniatis et al (Molecular Cloning, A Laboratory Manual, Cold Spring Harbor 1982).

The fragment was then ligated with the previously phosphorylated synthetic oligonucleotide and with the vector pSM214, digested with EcoRI and HindIII enzymes to remove the Bla gene.

The ligation reaction was carried out in the presence of the T4 DNA ligase enzyme by generally known techniques.

At the end of the enzymatic reaction, the entire mixture was used to transform E. coli cells made competent by treatment with CaCl$_2$ (Mandel M. and Higa (1970): J. Mol. Biol. 53, 154).

The transformed cells were then selected on a suitable culture medium, made selective by the addition of chloramphenicol, at a temperature of between 30° and 40° C. A hybrid plasmid containing the synthetic gene correctly inserted was thus isolated.

The plasmid (pSM274) was then used to transform Bacillus subtilis cells made competent by Contente and Dubnau's method (Mol. Gen. Genet 167, 258 (1979)).

To this end various strains of B. subtilis having the following characteristics (hpr$^-$ spr$^-$) may be used; in the present case was preferably used B. subtilis SMS 118 (rec$^+$, hpv$^-$, spr$^-$, Leu, pyrD1).

The transformed cells were then grown in a VY liquid medium (Veal Infusion Broth (DIFCO), Yeast extract (DIFCO)) with the addition of chloramphenicol, at a temperature of 37° C. or approximately 37° C.

The cells were then separated from the supernatant liquid by centrifuging, lysed accordingly to one of the generally known techniques and finally the lysates were analysed to determine the presence of the hGH precursor. In practice, the cell lysate was loaded anto a polyacrylamide gel and, after electrophoresis, the proteins were displayed either by staining with Coomassie blue (Gel Electrophoresis of Proteins: A Practical Approach edit. B. D. Hames and D. Rickwood IRL Press Limited) or by immunoblot (Towbin et al (1979), P.N.A.S., vol. 76 n. 9 4350–4354).

The results obtained showed the presence in the supernatant liquid of the cell lysis of a protein of approximately 23,000 daltons which migrates a little more slowly than the natural hGH control (Calbiochem) and which reacts with anti-hGH antibodies.

According to the present invention, the hGH precursor was then purified from the supernatant liquid of the cell lysate.

Known ion-exchange or IMAC chromatographic techniques were used for this purpose (Belew, M. et al (1987): Analytical Biochemistry 164, 457. The former, which uses anionic or cationic resin, makes use of the presence of the positive or negative charges of the acidic and/or basic amino acids present in the peptide extension to bind the hGH precursor to the column, whilst the second makes use of the affinity of histidine and other amino acids for some metal ions. In practice, after cell lysis and the separation of the lysed cells by centrifuging the supernatant liquid was loaded into a chromatographic column packed with a resin selected from DEAE cellulose or Sephadex, which binds the precursor strongly.

The proteins were then eluted from the column with the use of an eluent with an ionic gradient.

A buffer solution with an NaCl concentration of from 0.1 to 0.5M was preferably used.

It was thus possible to remove the precursor from the column with a yield greater than 90% and a purity of approximately 60%.

According to one embodiment of the method of the present invention, the protein suspension may be concentrated by the addition of up to 60% saturated ammonium sulfate so as to precipitate the proteins before the hGH precursor is purified. The proteins are then made soluble in a buffer and purified by means of ion-exchange chromatography or IMAC.

According to the present invention, the precursor thus purified was again suspended in a buffer and hydrolysed with Factor Xa, using a molar ratio of Factor Xa/hGH precursor of from ½ to 1/100.

The enzyme reaction was carried out at an ambient temperature (20°–25° C.) for the period necessary to bring the reaction to completion or almost to completion.

The reaction mixture was then dialysed against a buffer suitable for the subsequent chromatography and the mixture containing the mature hormone, any precursor which had not been hydrolysed, and the residual contaminant proteins, was again purified by ion-exchange chromatography or IMAC.

The residual protein and the precursor were thus bound to the column whilst the mature hormone, which was not retained, was eluted from the column with a yield > 90%.

Analysis of the amino acid sequences, carried out by the technique of Sanger F. et al (Proc. Natl. Acad. Sci. U.S.A. 74, 5463 (1977)), shows that the hormone thus purified has the correct sequence.

Moreover, upon electrophoretic analysis, the hormone shows a purity of 100% or approxiately 100%.

1: SMS 118 (pSM214) soluble proteinaceous fraction
2: SMS 118 (pSM214) insoluble proteinaceous fraction
3: SMS 118 (pSM274) soluble proteinaceous fraction
4: SMS 118 (pSM274) insoluble proteinaceous fraction
5: met-hGH
6: molecular weight standards.

Figure 3:

FIG. 3: WESTERN BLOT of the total of soluble and insoluble proteins of B. subtilis cells.

1: SMS 118 (pSM214) soluble proteinaceous fraction
2: SMS 118 (pSM214) insoluble proteinaceous fraction
3: SMS 118 (pSM274) soluble proteinaceous fraction
4: SMS 118 (pSM274) insoluble proteinaceous fraction
5: met-hGH.

The following examples are illustrative of the invention and are not limiting.

EXAMPLE 1

Construction of the hybrid plasmid pSM 274 a. Construction of the synthetic gene which codes for the precursor of hGH

The DNA sequence which codes for the human growth hormone (hGH) from amino acid 17 to amino acid 191 was isolated from the plasmid pSM209, described in Italian patent application no. 20345 A/86, by the treatment of the plasmid with FnuDII restriction enzyme, which cuts at the DNA level between amino acids 16 and 17, and HindIII enzyme, which cuts downstream of the stop codon.

For this purpose, 50 μg of pSM209 were cut with 50 units (U) of FnuDII (Biolabs) in 200 μl of a reaction mixture containing 6 mM Tris-HCl pH 7.4, 6 mM NaCl, 6 mM MgCl$_2$. 6 mM mercaptoethanol for 1 hour at 37° C.

After the enzyme had been deactivated at 70° C. for 10 minutes, the solution was brought to a concentration of 50 mM Tris-HCl pH 8.0, 10 mM MgCl$_2$, 50 mM NaCl and incubated at 37° C. for 1 hour in the presence of 50 U of HindIII (Boehringer).

After the enzyme had been deactivated at 70° C. for 10 minutes, the DNA was separated by the loading of the digestion mixture onto 6% acrylamide gel and the application of a voltage of 130 volts for 3 hours. The band of approximately 530 base pairs (bp), containing the sequence which codes for hGH from amino acid 17 to amino acid 191, was then eluted as described by Maxam and Gilbert (Methods in Enzymology vol. 65, 499–560 (1980)).

The fragment of DNA having the sequence given below was then synthesized by means of a System One DNA synthesiser (Beckman):

|  |  | Met | Glu | Glu | Leu | Met | Ile | Glu | Gly | Arg | Phe +1 | Pro +2 |
|---|---|---|---|---|---|---|---|---|---|---|---|---|
|  | 5'AATTCTT | ATG | GAA | GAA | CTT | ATG | ATC | GAG | GGT | AGG | AAG | GGT |
|  | GAA | TAC | CTT | CTT | GAA | TAC | TAG | CTC | CCA | TCC | TTC | CCA |
| +3 | +4 | +5 | +6 | +7 | +8 | +9 | +10 | +11 | +12 | +13 | +14 | +15 | +16 |
| Thr | Ile | Pro | Leu | Ser | Arg | Leu | Phe | Asp | Asn | Ala | Met | Leu | Arg |
| TGG | TAA | GGG | AAT | AGG | TCC | GAA | AAA | CTG | TTC | CGA | ATG | GAG | GGC |
| ACC | ATT | CCC | TTA | TCC | AGG | CTT | TTT | GAC | AAG | GCT | TAC | CTC | CCG |

Figure 1:
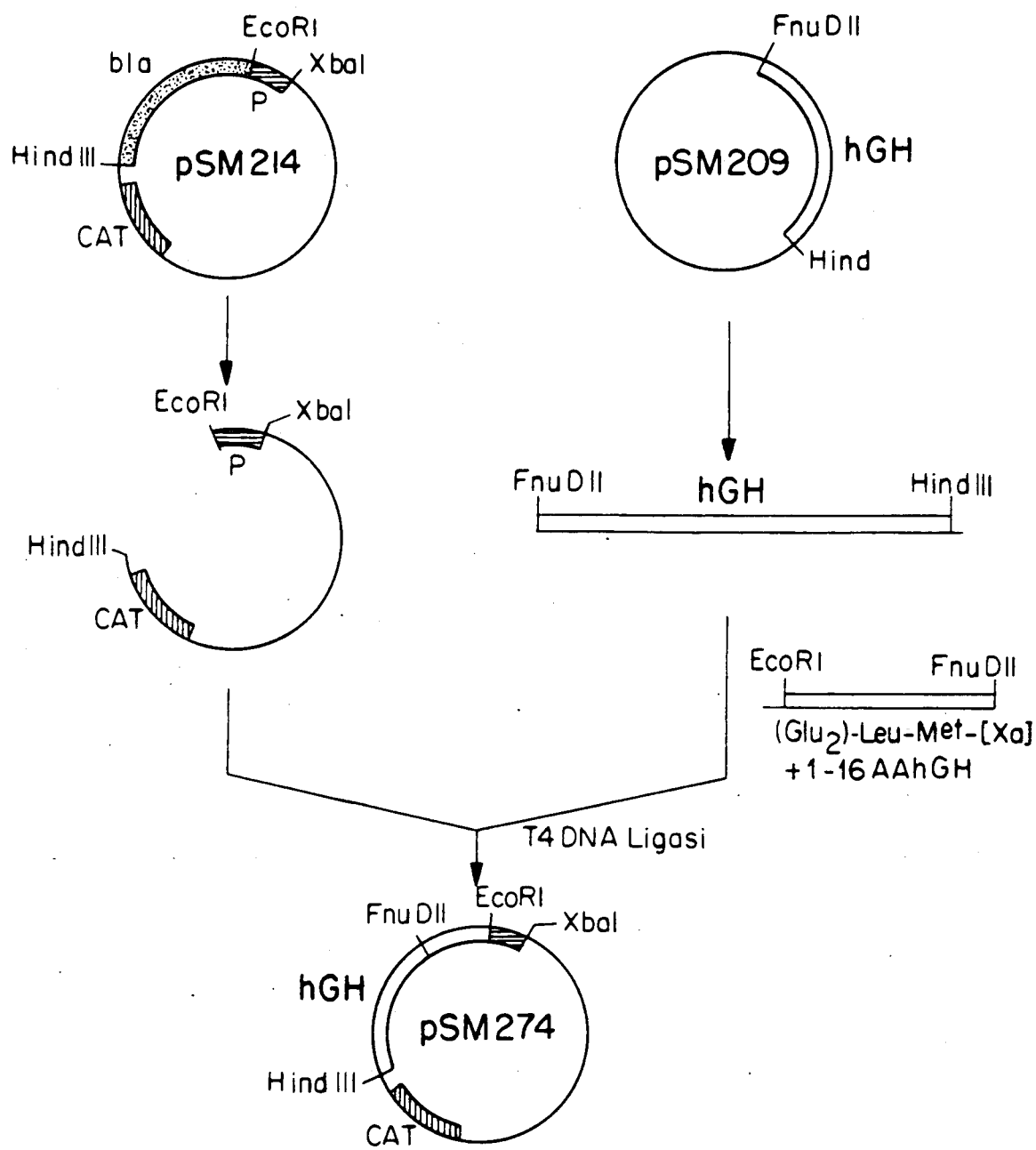
FIG. 1: a schematic representation of the construction of the plasmid pSM 274.

This DNA fragment codes for the first 16 amino acids of hGH and for the amino acids Met-Glu-Glu-Leu-Met-Ile-Glu-Gly-Arg, the latter being situated at the amino-terminal of the encoded peptide fragment. 1 μg of this DNA fragment was then phosphorylated in 10 μl of a buffer containing 66 mM Tris-HCl pH 7.5, 1 mM ATP, 1 mM spermidine, 10 mM MgCl$_2$, 15 mM dithiothreitol (DTT), 0.2 mg/ml of bovine serum albumin and 2 U of T4 kinase (Biolabs) for 1 hour at 37° C. and then the enzyme was deactivated at 65° C. for 10 minutes.

b. Construction of pSM 274 (FIG. 1)

2 μg of the plasmid pSM214 ATCC 67320 were digested in 20 μl of a buffer containing 50 mM Tris-HCl pH 7.5, 6 mM MgCl$_2$, 50 mM NaCl and 2 U respectively of EcoRI and HindIII at 37° C. for 1 hour. The enzymes were then deactivated by the digestion mixture being kept at 65° C. for 10 minutes and, immediately afterwards, the mixture was applied to a 0.8% agarose gel at 100 volts for 2 hours (Maniatis et al (1982), Molecular Cloning: A Laboratory Manual, Cold Spring Harbor).

The largest band of approximately 6500 bp was then eluted by known techniques (Maniatis et al (1982), Molecular Cloning: A Laboratory Manual, Cold Spring Harbor).

1.5 μg of the 6500 bp fragment, 400 ng of the 530 bp fragment of pSM209 and 50 ng of the synthetic fragment phosphorylated as described above), were then mixed in 150 μl of a buffer containing 66 mM Tris-HCl pH 7.6, 1 mM ATP, 10 mM MgCl$_2$, 10 mM DTT and ligated together in the presence of 2 U of T4 DNA ligase, at 14° C. for 18 hours. 5 μl of the ligation mixture were then used to transform 200 μl of commercially available *Escherichia coli E. coli* JM101 (BRL) cells made competent by teatment with 50 mM CaCl$_2$ (Mandel, M. and Higa (1970) J. Mol. Biol. 53, 154).

The transformants were then selected by spreading the cells on L agar medium plates (10 g/l Bacto Tryptone (DIFCO), 5 g/l Bacto Yeast extract (DIFCO) and 10 g/l NaCl) containing 20 μg of chloramphenicol (CM), at 37° C. for 12 hours.

From the Cm-resistant colonies, one was isolated which carried the required plasmid pSM724 (FIG. 1), whose nucleotide sequence was checked by the method of Sanger F. et al (Proc. Natl. Acad. Sci. USA 74, 5463 (1977).

Example 2

Expression of the synthetic gene which codes for the precursor of hGH in bacillus subtilis SMS118 *B. subtilis* cells (rec+, npr−, spr−, leu, pyrDI) made competent as described by Contente and Dubnau (1979) (Mol. Gen. Genet 167, 251–259) were transformed by the plasmid pSM274 and the transformants were selected on TBAB agar plates (Tryptose Blood Agar Base) containing 5 μg/ml of chloramphenicol.

Of 12 transformants analysed, only 7 were positive for the presence of the plasmid pSM274.

In order to verify the expression of the synthetic hGH gene in the SMS118 (pSM274) *B. subtilis* strain, these were grown in 10 ml of VY medium (Veal Infusion Broth (DIFCO) 25 g/l, Yeast Extract (DIFCO) 5 g/l) containing 5 μg/ml of chloramphenicol at 37° C. for 20 hours. 1 ml of the culture was then centrifuged (12,000 rpm×15 minutes), the cells were collected and washed twice with 5 ml of a buffer containing 30 mM Tris-HCl pH 7.5, 50 mM NaCl and then resuspended in 100 μl of ET buffer (20% sucrose, 50 mM Tris-HCl pH 7.6, 50 mM EDTA). 20 μl of a solution containing 5 mg/ml of lysozyme was then added to the suspension thus obtained and kept at 37° C. for 15 minutes. 130 μl of a buffer containing 125 mM Tris-HCl pH 6.8, 3% sodium dodecylsulfate (SDS), 3% beta-mercaptoethanol and 20% glycerol were then added to the mixture and the resulting mixture was kept at 95° C. for 3 minutes. 20 μl of cell lysate were applied to a 12.5% SDS-acrylamide gel (Laemmli; (1970) Nature, 277: 680) and after electrophoresis at 25 mA for 3 hours, the proteins were displayed either by dying with Coomassie Blue ("Gel Electrophoresis of Proteins: A Practical Approach" edit B. D. Hames and D. Rickwood, IRL Press Limited) or by transfer onto a nitrocellulose filter (Shleiher and Shull 45 μm pore size-Towbin).

The presence of hGH was shown by the treatment of the filter as described by Towbin et al. (P.N.A.S. 1979, Vol. 76 n. 9, 4350–4354) using rabbit anti-hGH antibodies (Miles) and goat anti-rabbit-IgG antibodies together with peroxidase (Miles).

Figure 2:
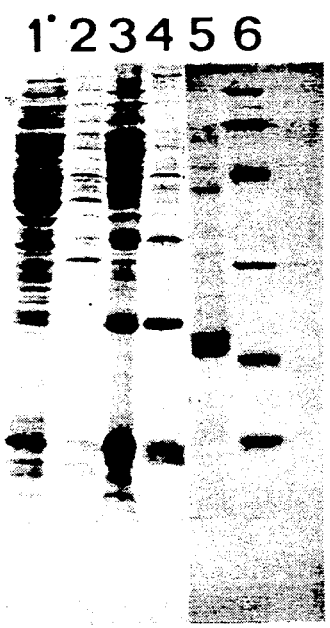
FIG. 2: SDS-PAGE stained with Coomassie-Blue containing the total of soluble and insoluble proteins from B. subtilis cells.

After staining with Coomassie Blue, a protein with an apparent molecular weight of approximately 23,000 daltons appears which therefore migrates more slowly than the natural hGH control (Calbiochem) and which represents approximately 6.2% of the total soluble proteins (FIG. 2).

The proteins react with anti-hHG antibodies as shown by immunoblot analysis (FIG. 3). The quantity of hGH precursor produced was estimated at 18 mg/liter when the stain was cultivated under laboratory conditions obtaining approximately 4 g of wet cell paste per liter of culture.

Example 3

Purification of the mature hGH

A) A culture of the SMS118 (pSM274) *B. subtilis* strain which had been glycerinated and kept at −80° C. was used to produce individual colonies of L agar plates containing 5 μg/ml of chloramphenicol. A colony was then used to innoculate 1 l of VY medium supplemented with 5 μg/ml of chloramphenicol. The culture was grown at 37° C. for 18 hours with agitation and then centrifuged at 7100 g for 10 minutes in a Sorvall centrifuge (GS3 rotor 6500 rpm) at 14° C. The cells thus recovered were resuspended in 12 ml of 10 mM Tris-HCl pH 8.0, 1 mM EDTA, 25% sucrose buffer and 3.2 ml of 0.5 EDTA pH 8.0 and 1 ml of a TE solution (10 mM Tris-HCL pH 8.0 1 mM EDTA) containing 40 mg/ml of lysozyme were then added. The suspension was incubated at 37° C. for 45 minutes and then, after transfer to an ice bath and the addition of phenylmethylsulphonyl-fluoride (PMSF) to a final concentration of 1 mM, was sonicated until a homogeneous suspension was obtained. The suspension was then centrifuged at 12,000 rpm for 30 minutes at 4° C. (Sorvall centrifuge, SS-34 rotor) and the supernatant liquid recovered and dialyzed extensively against a solution of 20 mM Tris-HCl pH 7.5, 1 mM PMSF.

B) Ion-exchange chromatography. A 20×1.6 cm column of DEAE cellulose (Whatman DE 52) was equilibrated with 30 mM Tris-HCl, 1 mM PMSF pH 7.5 at 4° C. (flow rate 30 ml/hour) and then loaded with the proteinaceous solution prepared as in step A). After the column had been washed with three volumes of equilibrating buffer, it was eluted with 200 ml of 0.1 mM NaCl, 20 mM Tris-HCl pH 7.5 buffer. This saline concentration is sufficient to elute approximately 90% of the fused protein. A subsequent washing with 20 mM Tris-HCl, 0.5M NaCl pH 7.5 removes the remaining proteins.

C) Ion-exchange chromatography. The fractions containing the fused proteins were recombined and dialyzed against a 20 mM NaHPO$_4$/Na$_2$HPO$_4$ pH 6.7 buffer and then loaded into a 15×1 cm column of DEAE cellulose equilibrated with the same buffer. After the proteins which were not retained had been washed out, the fused protein was eluted with 0.1M NaCl in the equilibrating buffer. The fractions containing the hGH precursor were recovered and ammonium sulfate (60% saturated) was added to precipitate the total proteins present. The precipitate was then recovered and dissolved in 6 ml of 50 mM Tris-HCl pH 8.0, 100 mM NaCl and 1 mM $CaCl_2$ solution. Blood Factor Xa protease prepared and purified as described by Theogersen H. C. (1978) (Biochem. J. 175, 613) was then added to the solution in a Factor Xa/hGH precursor molar ratio of 1:10. The enzyme reaction was carried out with the mixture being kept at ambient temperature (20°–25° C.) for 24 hours. 90% of the hGH precursor were thus digested and converted into the hormone having the natural sequence, as shown by analysis of the first ten amino acids carried out with a System 80 Sequencer (Beckman). In order to remove the excess salts, the sample was extensively dialyzed against pH 6.7 $NaH_2PO_4/Na_2HPO_4$ 20 mM buffer.

D) Purification of the natural hGH. The method described in step C) was used. Under these conditions, unlike the contaminating proteins and any precursor not digested by the Factor Xa which can be eluted by an increase in the concentration of NaCl in the elution buffer to 100 mM, the natural human growth hormone was not retained by the column. The hGH thus obtained was 98% pure. The purity of the hGH can be increased to values of 100% or approximately 100% by its subsequent passage through a RP-HPLC($C_3$) column and elution with an acetonitrile gradient. The exact sequence of hGH was verified by the determination of the amino-terminal sequence with the use of 50 μg of pure hGH and a Model 890A Beckman automatic sequencer. The phenyl thio hydantoine (PTH) aminoacids were analysed by the method described by Hawke D. et al Anal. Biochem. 120, 302 (1982) slightly modified by us. As expected the sequence of the first ten amino acids was: Phe Pro Thr Ile Pro Leu Ser Arg Leu Phe.

We claim:

1. A method for the preparation of a substantially pure protein having the sequence of naturally occurring human growth hormone comprising the steps of:
   (A) transforming *Bacillus subtilis* cells with a hybrid plasmid comprising a gene encoding a precursor of human growth hormone, wherein said precursor of human growth hormone contains, at the N-terminal of naturally occurring human growth hormone, the following amino acid sequence:

$(aa)_n$-Idle-Glu-Gly-Argwherein:
   $(aa)_n$ is

Met-Glu-Glu-Leu-Met;

wherein Ile-Glu-Gly-Arg- is the tetrapeptide recognized by Factor Xa;
   (B) culturing the resulting transformed cells of step (A) such that they synthesize said precursor of human growth hormone;
   (C) lysing the resulting cultured transformed cells of step (B) and recovering the supernatant liquid containing said precursor of human growth hormone;
   (D) purifying the resulting precursor of human growth hormone from the resulting supernatant liquid of step (C) by chromatography;
   (E) hydrolyzing the resulting precursor of human growth hormone of step (D) by treatment with Factor Xa to produce a protein having the sequence of naturally occurring human growth hormone; and
   (F) purifying the resulting protein having the sequence of naturally occurring human growth hormone of step (E) from the resulting hydrolysis mixture by chromatography so as to obtain said substantially pure protein having the sequence of naturally occurring human growth hormone.

2. The method according to claim 1, wherein the strain of *Bacillus subtilis* in step (A) is *B. Subtilis SMS*118.

3. The method according to claim 1, wherein the hybrid plasmid of step (A) is obtained by:
   (i) digesting the expression vector pSM214(ATCC No. 67320) with EcoRI and HindIII;
   (ii) ligating the resulting EcorRI- and HindII-digested expression vector to the gene which encodes the precursor of human growth hormone such that the precursor of human growth hormone is expressed by said hybrid plasmid when said cells are transformed with said hybrid plasmid.

4. The method according to claim 1, wherein the purification in steps (D) and (F) is carried out by ion-exchange chromatography or immobilized metal affinity chromatography.

5. The method according to claim 1, wherein the hydrolysis in step (E) is carried out at 20° to 25° C. using a Factor Xa/precursor molar ratio of from ½ to 1/100.

* * * * *